United States Patent [19]

Taylor

[11] Patent Number: 4,943,316

[45] Date of Patent: Jul. 24, 1990

[54] RELATING TO THE FORMATION OF METAL ALKOXIDES AND METAL POWDERS BY THE USE OF MICROWAVE RADIATION

[75] Inventor: Reginald M. Taylor, Hawthorn, Australia

[73] Assignee: Hallsworth & Associates Pty. Limited, Keswick, Australia

[21] Appl. No.: 266,634

[22] PCT Filed: Dec. 24, 1987

[86] PCT No.: PCT/AU87/00443

§ 371 Date: Aug. 30, 1988

§ 102(e) Date: Aug. 30, 1988

[87] PCT Pub. No.: WO88/05035

PCT Pub. Date: Jul. 14, 1988

[30] Foreign Application Priority Data

Dec. 30, 1986 [AU] Australia ............................... PH9697

[51] Int. Cl.$^5$ ................................................ B22F 9/16
[52] U.S. Cl. ................................. 75/0.5 A; 204/157.43
[58] Field of Search ........................................ 75/0.5 A

[56] References Cited

U.S. PATENT DOCUMENTS

| | | | |
|---|---|---|---|
| 4,431,164 | 2/1984 | Jungo | 75/0.5 A |
| 4,544,761 | 10/1985 | Taylor et al. | 514/844 |
| 4,755,369 | 7/1988 | Yoshiharu | 75/0.5 A |

FOREIGN PATENT DOCUMENTS 2494583 5/1982 France .
2101132 1/1983 United Kingdom .

OTHER PUBLICATIONS

Hambley et al., The Crystal and Molecular Structure of Zinc(II) Monoglycerolate, Aust. J. Chem., 1983, v. 36, pp. 1249–1253.
Radoslovich et al., Crystalline Cobalt, Zinc, Manganese, and Iron Alkoxides of Glycerol, in Australian J. of Chem., 1970, V. 23, pp. 1963–1971.

Primary Examiner—Peter D. Rosenberg

[57] ABSTRACT

The method of forming metal alkoxides and metal powders which consists in the formation and elimination of water or equivalent compounds and the resultant production of a metal alkoxide or metal powder in which particular metal compounds when in a solution or suspension are subjected to molecular bond excitation by microwave radiation.

19 Claims, 1 Drawing Sheet

RELATING TO THE FORMATION OF METAL ALKOXIDES AND METAL POWDERS BY THE USE OF MICROWAVE RADIATION

BACKGROUND OF THE INVENTION

This invention relates to the formation and elimination of water or an equivalent compound and the resultant production of a metal alkoxide from a solution or suspension of particular metal compounds in a suitable polyhydric alcohol by a reaction initiated and maintained by the absorption of microwave radiation.

Examples of this invention are given by the formation of metal alkoxides of propanetriol (glycerolates) when particular compounds of these metallic elements such as zince or bismuth are mixed with or dissolved in glycerol and the resultant solution or suspension is irradiated by microwave energy of a suitable wavelength. The reactions involved may be exemplified by chemical equations showing the formation of zinc glycerolate (Zinc(1,2,3-propanetriolato(2-)-☐1, ☐2) homopolymer, stereoisomer; $C_3H_6O_3Zn$) from a suspension of zinc hydroxide (or a solution of zinc acetate) in glycerol (propanetriol, $C_3H_8O_3$):

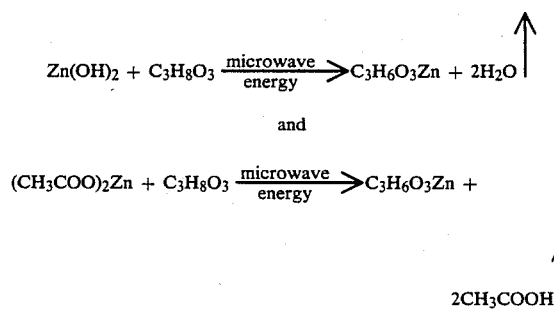

A further example of the invention may be given by the formation of a new crystalline metal-organic compound, when, zinc hydroxide is reacted with the polyhydric alcohol sorbitol ($CH_2OH-(CHOH)_4-CH_2OH$).

The invention is not limited to the compounds of these elements or to the alcohols glycerol and sorbitol but extends to and embraces any other element whose particular compounds may be reacted with a di-, tri-, or poly-hydric alcohol by these microwave techniques.

The high temperature formation of the glycerolates of zinc, cobalt, manganese and iron has already been described, (1) Australian Journal of Chemistry vol. 23 no. 10, p1963 1971, Radoslovich, E. W., Raupach, M., Slade, P. G. and Taylor, R. M.

(2) Clays and Clay Minerals vol. 18 (1970), p53–62, Fuls, P. F., Rodrique, L. and Fripiat, J. J.

(3) Australian Journal of Chemistry vol. 36 (1983) p 1249–1253, Hambly, T. J. and Snow, M. R.

These reactions are achieved by the direct heating of particular oxides or hydroxides or other suitable compounds or salts of these metallic elements in the polyhydric alcohol, glycerol.

The pharmaceutical, cosmetic and various industrial applications of the zinc glycerolate, formed by the reaction of certain zinc compounds with glycerol at elevated temperatures, are the subjects of previous patents granted and applied for namely:

U.K. Letters Patent No. 2101132 May 15, 1985, R. M. Taylor and A. J. Brock.

Letters Patent France 81 21 914 Nov. 23, 1981, R. M. Taylor and A. J. Brock.

U.S. Pat. No. 4,544,761 Oct. 1, 1985, R. M. Taylor and A. J. Brock.

SUMMARY OF THE INVENTION

The present invention relates to the formation and elimination of water or an equivalent compound and the resultant production of a metal alkoxide from a solution or suspension of particular metal compounds in a suitable polyhydric alcohol by a reaction initiated and maintained by the absorption of microwave radiation.

The present invention specifically relates to an improved method of forming these high-temperature glycerolate compounds by the use of a new technique whereby the absorption of radiated microwave energy of a suitable wavelength causes some nearby C—OH groups to condense to form

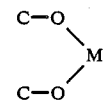

linkages, plus water, where M denotes a a metal capable of taking part in such a reaction. The formation of an alkoxide or its degree of crystallinity may be limited by steric hindrances imposed by the size of the metallic cation or by other factos, such as its coordination requirements.

Thus, it is believed that, in the presence of particular, suitable metallic oxides, hydroxides, oxyhydroxides or metallic oxy-salts that thermally decompose into the fine-grained metallic oxide at temperatures below the boiling or decomposition temperature of the alcohol being used, the excitation of the OH groups of the polyhydric alcohol may lead to the coordination of the metal through oxygen ligands to form the alkoxide, with the associated formation and elimination of water.

However, it is noted that a reaction which may proceed rapidly and efficiently when an aqueous suspension of the metal hydroxide is used, may be inhibited if, for example, the oxide or some particular oxide phase of the metal is used instead. Furthermore, it is known within the scope of this invention that for the same band-width of wavelengths of the incident microwave energy, particular metal alkoxides may only by induced to form or form efficiently when a suitable compound of the metal, rather than its oxide or hydroxide form, it used.

This invention is meant to embrace an alteration of the wavelength band-width of the incident microwave radiation where such a variation may enable the formation of an alkoxide to proceed, or to proceed more efficiently, or to proceed with a desired modification of the properties of the alkoxide.

The scope of this invention also includes the application of microwave energy to suspensions or solutions of the compounds of certain metals in polyhydric alcohols where, in some cases, as will be exemplified, the metal alkoxide is not the preferred end product of the reaction induced by the irradiation, but rather, a fine-grained, generally crystalline precipitate of the pure metallic phase may be formed by reductive processes.

Therefore, the technique of this invention may be said to offer an improvement in the method of formation of some of the metal alkoxides. Moreover, where a metallic alkoxide is not formed and the reaction results in the formation of metallic powders, the technique of the invention offers an improvement in the production of these metallic powders from a reaction between particular metal compounds and an alcohol.

Examples of the improvement in the method of formation of an alkoxide or metallic powders by the technique of this invention are given. By subjecting a suspension of zinc hydroxide in an excess of glycerol to microwave radiation in a normal domestic microwave cooking apparatus, very well crystalline zinc glycerolate forms within a few minutes. The improvement in the quality of the crystalline alkoxide so formed may be exemplified by the electron microgrphs which form part of this document and in which the variation in size and morphology of zinc glycerolate crystals in shown.

DETAILED DESCRIPTION

Figure 1:
FIG. 1 is a scanning electron microscope-produced photomicrograph showing crystals as prepared by the conventional technique of heating and suspension of zinc oxide in glycerol.

The form of crystal shown in FIG. 1 was the result of prolonged heating with constant stirring, and a similar formation resulted when the prolonged heating was carried out under reduced pressure.

Figure 2:
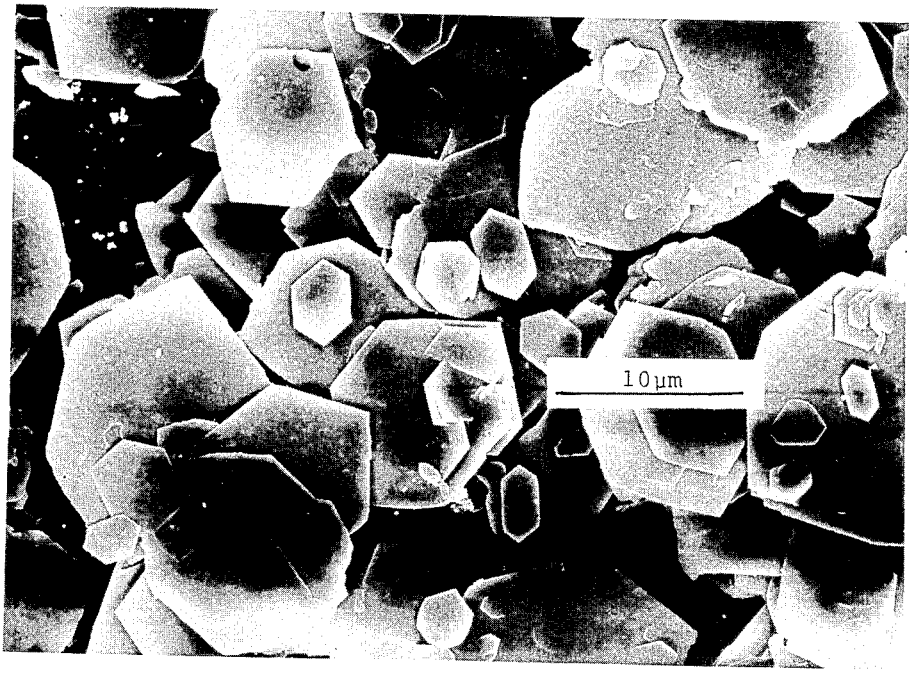
FIG. 2 is a scanning electron microscope-produced photomicrograph showing result of subjecting suspension of zinc hydroxide in glycerol to microwave radiation for a few minutes in accordance with the method of the present invention.

In reference to the scanning electron micrographs, it will be of interest to note that crystals as shown in FIG. 1 which result from prior art methods of production, are of less regular form than the crystals shown in FIG. 2, produced by the method of this invention, and, further, it is to be noted that the crystals of this invention have a regular hexagonal shape, irrespective of size, unlike the prior art crystals.

The glycerolate crystals shown have a substantial extension in two planes but low thickness, and because of the regular crystalline configuration and substantial variation in extension in two planes, have high covering capacity when similarly orientated and also have substantial lubricity because of the uniformity of the hexagonal crystal formation.

It is believed that the microwave action of the present invention induces significant vibration in particular molecular bonds, which accelerates and enhances the reaction.

It will be appreciated from the photomicrographs that the zinc glycerolate prepared by the conventional technique of heating zinc oxide with glycerol produces irregular crystals, whereas, when microwave radiation is applied, a much uniformly crystalline structure results, and regular particle production results from a suspension of zinc hydroxide in glycerol.

It has been found that improvements offered by the technique of this invention apply in a wide field. An example is the reaction induced by such microwave energy between a suspension of basic cooper carbonate in glycerol or ethylene glycol or a solution of copper acetate in glycerol, according to which the formation of micron-sized hexagonal copper crystals was found to exist.

Further examples of the technique are given by the production of crystalline metallic bismuth by a microwave energy-induced reaction between a concentrated aqueous suspension of BiOCl admixed with sorbitol, but reference to these examples does not in any way limit the scope of this invention to the initial metallic compounds or the polyhydric materials stated in examples.

Futher improvements arising out of the technique of this invention are:

firstly, the reduction in time of formation, secondly, a greater measure of control of the reaction between the metal compound and the alcohol, and thirdly, a reduced chance of ignition during the formation of the metal alkoxide or metallic microcrystals.

Again without limiting the scope of this invention, examples are given for the formation of metal alkoxides by the technique of inducing and maintaining the reaction by the use of absorpition of microwave energy, each of these subjecting a metal source in the presence of a glycerol to the action of microwaves.

EXAMPLE 1

Manganese glycerolate was formed by the addition of one gram of manganese (II) acetate to ten millilitres of glycerol and one millilitre of distilled water and then reacting this solution-suspension in a domestic microwave oven (National model NE-8070, 650 watts) for six minutes at the medium power setting of the microwave oven. The resulting pinkish-white precipitate in the glycerol residues was cooled, washede with ethyl alcohol and dried at 105° C. The dried, pinkish-white powder was highly crystalline and exhibited a high degree of lubricity.

EXAMPLE 2

Cobalt glycerolate was formed by dissolving cobalt acetate in an excess of glycerol (1:10) by gentle heating and then adding a small amount of NaOH. The solution was then subjected to absorption of microwave energy and a purple precipitate formed on washing and drying from ethanol, the magenta-coloured, highly lubricious crystalline precipitate was identified as the cobalt glycerolate originally described.

EXAMPLE 3

Bismuth glycerolate was formed by a reaction initiated by subjecting a suspension or solution of particular bismuth compounds in glycerol to microwave radiation.

A crystalline alkoxide was formed by dispersing 1-2 g bismuth subnitrate in 20 ml glycerol and subjecting the suspension to microwave energy (3 minutes on medium settin (National model Genius). On cooling, the greyish-white crystalline powder was washed and dried from ethanol.

EXAMPLE 4

Iron glycerolate was formed by subjecting a suspension of freshly precipitated ferric hydroxide (ferrihydrite) in excess glycerol (ratio approx 1:10) to microwave radiation. The green cyrstalline powder contained both divalent and trivalent iron and the relative amounts of these two cations caused a variation in colour, the crystalline structure and the composition.

The claims defining the invention are as follows:

I claim:

1. A process for thermally decomposing a metallic compound using microwave energy, comprising:
   (a) providing a metallic compound selected from the group consisting of a metallic oxide, metallic hydroxide, metallic oxydroxide and metallic oxy-salt, that is capable of thermally decomposing to form a fine-grained metal or metal alkoxide at a temperature below the lower of the boiling point and decomposition temperature of a given di-, tri- or polyhydric alochol;
   (b) dissolving and/or suspending said metallic compound in an excess of said given di-, tri- or polyhydric alcohol;
   (c) subjecting the solution and/or suspension thus formed to irradiation by microwave energy, whereby said metallic compound is reacted to form a fine-grained metal or metal alkoxide.

2. The process of claim 1, wherein:
   step (c) is conducted by subjecting the solution and/or suspension thus formed to irradiation using microwave energy within a range of frequencies characteristic of a household microwave of a type used by consumers for food preparation.

3. The process of claim 1, wherein:
   said metallic compound is one selected from the group consisting of zinc hydroxide, zinc acetate, copper carbonate, copper acetate, BiOCl, bismuth subnitrate, manganese II acetate, cobalt acetate and ferric hydroxide.

4. The process of claim 3, wherein:
   said di-, tri- or polyhydric alcohol is an alcohol selected from the group consisting of glycerol, sorbitol and ethylene glycol.

5. The process of claim 4, wherein:
   said metallic compound is manganese II acetate, said alcohol is glycerol, and said solution and/or suspension further includes water.

6. The process of claim 4, wherein:
   said metallic compound is cobalt acetate, said alcohol is glycerol, and said solution and/or suspension further includes NaOH.

7. The process of claim 1, wherein:
   said metallic compound is zinc hydroxide, said alcohol is glycerol, and conducting step (c) results in production of zinc glycerolate.

8. The process of claim 1, wherein:
   said metallic compound is zinc acetate, said alcohol is glycerol, and conducting step (c) results in production of zinc glycerolate.

9. The process of claim 1, wherein:
   said metallic compound is zinc hydroxide, said alcohol is sorbitol, and conducting step (c) results in production of zinc.

10. The process of claim 1, wherein:
    said metallic compound is copper carbonate, said alcohol is glycerol, and conducting step (c) results in production of copper.

11. The process of claim 1, wherein:
    said metallic compound is copper carbonate, said alcohol is ethylene glycol, and conducting step (c) results in production of copper.

12. The process of claim 1, wherein:
    said metallic compound is copper acetate, said alcohol is glycerol, and conducting step (c) results in production of copper.

13. The process of claim 1, wherein:
    said metallic compound is BiOCl, said alcohol is sorbitol, and conducting step (c) results in production of bismuth.

14. The process of claim 1, wherein:
    said metallic compound is manganese II acetate, said alcohol is glycerol, and conducting step (c) results in production of manganese glycerolate.

15. The process of claim 1, wherein:
    said metallic compound is cobalt acetate, said alcohol is glycerol, and conducting step (c) results in production of cobalt glycerolate.

16. The process of claim 1, wherein:
    said metallic compound is bismuth subnitrate, said alochol is glycerol, and conducting step (c) results in production of bismuth glycerolate.

17. The process of claim 1, wherein:
    said metallic compound is ferric hydroxide, said alcohol is glycerol, and conducting step (c) results in production of iron glycerolate.

18. A fine-grained metal produced by the process of claim 1.

19. A fine-grained metal alkoxide produced by the process of claim 1.